United States Patent [19]
Granberg et al.

[11] Patent Number: 5,648,483
[45] Date of Patent: Jul. 15, 1997

[54] CONTINUOUS TRANSESTERIFICATION METHOD FOR PREPARING POLYOL POLYESTERS

[75] Inventors: Eric Paul Granberg; Richard Gerard Schafermeyer, both of Cincinnati; James Anthony Letton, Forest Park, all of Ohio

[73] Assignee: The Procter & Gamble Company, Cincinnati, Ohio

[21] Appl. No.: 481,779

[22] Filed: Jun. 7, 1995

[51] Int. Cl.$^6$ ............................................. C07H 1/00
[52] U.S. Cl. ........................ 536/119; 536/115; 554/167; 554/168
[58] Field of Search ......................... 536/119, 115, 536/167, 168

[56] References Cited

U.S. PATENT DOCUMENTS

| | | | |
|---|---|---|---|
| 2,383,633 | 8/1945 | Trent | 536/119 |
| 3,496,159 | 2/1970 | Spence | 260/97.6 |
| 4,431,838 | 2/1984 | Feldman et al. | 560/234 |
| 4,435,595 | 3/1984 | Agreda et al. | 560/234 |
| 4,517,360 | 5/1985 | Volpenheim | 536/119 |
| 4,668,439 | 5/1987 | Billenstein et al. | 554/167 |
| 4,847,430 | 7/1989 | Quang et al. | 568/697 |
| 4,895,971 | 1/1990 | Su | 558/346 |
| 4,976,892 | 12/1990 | Jeromin et al. | 260/410.7 |
| 5,079,355 | 1/1992 | Meszàros Grechke et al. | 536/119 |
| 5,254,722 | 10/1993 | Peukert et al. | 554/227 |

FOREIGN PATENT DOCUMENTS

| | | |
|---|---|---|
| 0523767 | 1/1993 | European Pat. Off. |
| 2503195 | 7/1976 | Germany . |
| A-3515403 | 10/1986 | Germany . |
| 2109265 | 6/1983 | United Kingdom . |
| 2174697 | 12/1988 | United Kingdom . |

OTHER PUBLICATIONS

U. R. Kreutzer, *Manufacture of Fatty Alcohols Based on Natural Fats and Oils*, Jaocs, vol. 61, No. 2 (Feb. 1984) pp. 343–348.

Kirk Othmer, Encyclopedia of Chemical Technology, vol. 9, 755–781 (4th Ed., 1994).

Kirk Othmer, Encyclopedia of Chemical Technology, vol. 1, pp. 878–885 (4th Ed., 1994).

G. Astarita et al., *Gas Absorption and Desorption with Reversible Instantaneous Chemical Reaction*, Chemical Engineering Science vol. 35, pp. 1755–1764.

G. Astarita, List of Publications, Chem. Eng. Sci., vol. 49, No. 5, pp. 575–580. (1994).

*Gas Absorption and Desorption with Reversible Instantaneuos Chemical Reaction*, Chemical Engineering Science, vol. 47, No. 8, pp. 2125–2127 (1992).

P. V. Danckwerts et al., *The Absorption of Carbon Dioxide into Solutions of Alkalis and Amines*, Chemical Engineer, Review Series No. 2, (Oct., 1966).

Yu et al., *Design of Packed Towers for Selective Chemical Absorption*, Chemical Engineering Science, vol. 42, No. 3, pp. 425–433 (1987).

H. Sawistowski et al., *Performance of Esterification in a Reaction–Distillation Column*, Chemical Engineering Science, vol. 43, No. 2, pp. 355–360 (1988).

E.P. Granberg, Ser. No. 08/486847, filed Jun. 7, 1995.

*Primary Examiner*—Elli Peselev
*Attorney, Agent, or Firm*—Daniel F. Nesbitt; Rose Ann Dabek; J. C. Rasser

[57] ABSTRACT

Polyol polyesters can be made by a transesterification reaction of a polyol with a lower alkyl fatty acid ester. A by product of that reaction are the alcohols from the lower alkyl esters. These are usually removed from the transesterification reaction by inert gas stripping. The process herein links the transesterification reaction with a lower alkyl ester formation reaction. The transesterification reaction acts as a the source of the lower alkyl alcohols for the formation of the lower alkyl esters used in the polyol fatty acid polyester synthesis. A preferred method for both reactions uses a reactive absorption column.

19 Claims, 2 Drawing Sheets

CONTINUOUS TRANSESTERIFICATION METHOD FOR PREPARING POLYOL POLYESTERS

TECHNICAL FIELD

This is a continuous process for preparing polyol polyesters using a transesterification reaction. The transesterification polyester formation reaction can be coupled with a process to make a lower alkyl, e.g., methyl, esters of fatty acids which uses the gaseous alcohols derived from the transesterification reaction as a source of the lower alkyl alcohols.

BACKGROUND OF THE INVENTION

Certain polyol fatty acid polyesters have been suggested as low or reduced calorie substitutes for triglyceride fats and oils used in foods. For example, nonabsorbable, nondigestible sugar fatty acid esters or sugar alcohol fatty acid esters having at least 4 fatty acid esters groups with each fatty acid having from 8 to 22 carbon atoms have been used as partial or full fat replacers in low calorie food compositions. See Mattson and Volpenhein; U.S. Pat. No. 3,600,186; Issued Aug. 17, 1971. Likewise, certain intermediate melting polyol polyesters have been developed that provide passive oil loss control, while at the same time reducing waxiness in the mouth. See Bernhardt; European Patent Application Nos. 236,288 and 233,856; Published Sep. 9, and Aug. 26, 1987, respectively. Blends of completely liquid polyol polyesters with completely solid polyol polyester hardstocks, preferably esterified with $C_{10}$ to $C_{22}$ saturated fatty acids (e.g. sucrose octastearate) have also been proposed. Other blends of liquid polyol polyesters and solid nondigestible fats are also known. See for example, Elsen et al, U.S. Pat. No. 5,422,131, 1995, Jandacek; U.S. Pat. No. 4,005,195; and Jandacek/Mattson; U.S. Pat. No. 4,005,196; Both issued Jan. 25, 1977.

A number of different processes have been disclosed in the art for preparing these highly esterified polyol fatty acid polyesters, in particular sucrose polyesters. One such process involves a solvent-free, essentially two-step transesterification of the polyol (e.g., sucrose) with the fatty acid esters of an easily removable alcohol (e.g., fatty acid methyl esters). In the first step, a mixture of sucrose, methyl esters, alkali metal fatty acid soap and a basic esterification catalyst are heated to form a melt. The amount of methyl esters used is such that the melt forms primarily partial fatty acid esters of sucrose, e.g., sucrose mono-, di- and/or triesters. In the second step, an excess of methyl esters are added to this melt which is then heated to convert the partial sucrose esters to more highly esterified sucrose polyesters, e.g., sucrose hexa-, hepta-, and particularly octaesters. See, for example, U.S. Pat. No. 3,963,699 (Rizzi et al.), issued Jun. 15, 1976; U.S. Pat. No. 4,517,360 (Volpenhein), issued May 14, 1985; and U.S. Pat. No. 4,518,772 (Volpenhein), issued May 21, 1985, which disclose solvent-free, two-step transesterification processes for preparing highly esterified polyol fatty acid polyesters, in particular highly esterified sucrose polyesters.

In some processes for preparing highly esterified polyol fatty acid polyesters, all of the fatty acid methyl esters are added to the polyol (e.g., sucrose) at the beginning of the reaction, i.e. a one-step addition process. See, for example, U.S. Pat. No. 4,611,055 (Yamamoto et al.), issued Sep. 9, 1986. Like the two-step processes, partial fatty acid esters of sucrose are formed first and are then converted to more highly esterified sucrose polyesters. Accordingly, these single-step and two-step processes are collectively referred to hereinafter as "two-stage" transesterifications, wherein the "first stage" involves the formation of the partial esters and wherein the "second stage" involves the conversion of the partial esters to more highly esterified polyesters.

Alternatively, highly esterified polyol polyesters may be prepared by two stage solvent-based processes, (see, for example, U.S. Pat. No. 4,954,621 issued to Masaoka et al.), or one stage solvent-based or solvent free processes, see for example, U.S. Pat. No. 4,968,791, (Van Der Plank), issued Nov. 6, 1990; U.S. Pat. No. 5,079,355 (Meszaros Grechke et al.) issued Jan. 7, 1992; or U.S. Pat. No. 5,071,975 (Ver der Plank et al.) issued Dec. 10, 1991.

The methyl esters used to prepare polyol polyesters can be prepared by the transesterification of triglyceride oils and fats with methanol in the presence of an alkaline catalyst. After the transesterification reaction, a crude glycerine layer comprising glycerine formed in the transesterification reaction, soap formed by the catalyst, catalyst, some methyl esters and methanol, is separated from the fatty-acid methyl ester layer. The methyl ester layer is then purified by any suitable recovery method, such as, e.g., distillation. Processes of this type have been described in U.S. Pat. Nos. 2,383,596, 2,383,579, 2,383,580, 2,383,596, 2,383,599, 2,383,601, 2,383,602, 2,383,614, 2,383,632 and 2,383,633 and in the European Patent 0 164 643. An extra esterification step before recovery, but after separation of the fatty acid methyl ester layer from the glycerol layer may optionally be used to produce high yields of high purity fatty acid methyl esters. See European Patent 391 485.

Methyl esters are a cheaper carboxylic acid source than acid chlorides or anhydrides, and they are sufficiently reactive to provide a good source of fatty acids for complex esterification reactions. The economics of the reactions are such that the relatively inexpensive cost of methyl esters outweighs any added processing costs. The lower alkyl alcohol group is chosen because the alcohol can be easily removed in the subsequent transesterification reaction through vacuum distillation or reducing the partial pressure of the alcohol using a nitrogen or inert gas sparge, forcing the transesterification reaction to completion.

Typically, methyl esters of fatty acids are prepared from the naturally occurring fatty acids sources, usually triglycerides from vegetable or animal sources. The methyl alcohol replaces the glycerine. The resultant mixture of methyl esters are easily fractionated, providing a purified source of fatty acids.

In a standard polyol polyester synthesis of this type, the polyol is reacted with a lower alkyl fatty acid ester in the presence of a catalyst and under an inert atmosphere. The inert gas stream from this transesterification reaction contains the released lower alkyl alcohol which is removed continuously from the reaction to drive the polyol polyester synthesis to completion. The transesterification reaction can be coupled with another transesterification process to make a lower alkyl, e.g., methyl, esters of fatty acids through a reaction using gaseous alcohols derived from the polyol polyester synthesis reaction as a source of the lower alkyl alcohols.

It has been found that the alcohol, diluted with nitrogen or other inert gas carrier can be reacted with a fatty acid ester, preferably a triglyceride, to form the corresponding methyl or lower alkyl fatty acid ester in a very efficient process. Preferably the reaction is run in a reactive adsorption column, but it can be done in a batch process. The recovered inert gas sparge from the polyol polyester synthesis is used to make the starting methyl esters for the synthesis. At the same time, over 90%, and up to 99.7%, of the methanol is removed from the inert gas stream. The alcohol free or reduced alcohol nitrogen (inert gas).can then be continuously recycled to the polyol polyester synthesis. This ability to recycle nitrogen significantly improves the economics of these reactions.

A key economic driver for this process is the integration or close coupling of methyl ester synthesis and transesterification reactions which use these esters as a fatty acid or carboxylic acid source. Traditionally methanol can be recovered from the inert gas stream by condensation, absorption into organic solvents, (e.g. triethylene glycol) or adsorption onto activated carbon. This reaction when coupled with a polyol polyester synthesis eliminates a separate methanol recovery system, eliminates handling of methanol and partially reduces the discharge of methanol into the environment.

It is an object of this invention to provide an improved method for making polyol polyesters. It is a further object of this invention to provide a method for making methyl esters of fatty acids through a transesterification reaction using gaseous methanol in a reactive adsorption column which is coupled with a polyol polyester synthesis.

SUMMARY OF THE INVENTION

A process for preparing polyol polyesters wherein the alkyl ester synthesis and the polyol polyester synthesis are coupled is claimed. The reaction comprises the steps of reacting a triglyceride or other fatty acid source with a gaseous mixture of an inert gas and lower alkyl alcohol at a temperature of between about 20° C. to about 100° C., at a pressure of about 14 to about 150 psia (pounds per square inch absolute pressure) in the presence of a catalyst. The molar ratio of methanol to triglyceride is in the range of 0.1:1 to about 15:1. The alkyl esters are separated from the glycerine by centrifugation or other separation technique and from the mono-and diglycerides by fractionation, as conventionally practiced in the art. The purified stream of inert gas is recovered which is used as the sparging gas in a polyol polyester synthesis in which a polyol is reacted with the recovered methyl ester from the first step in a solvent-free two-stage process which comprises forming polyol fatty acid partial esters from a reaction mixture containing and fatty acid esters of an easily removable alcohol in the presence of an effective amount of a basic catalyst and optionally an effective amount of soap emulsifier, and wherein said second stage comprises forming highly esterified polyol fatty acid polyesters from a reaction mixture containing the polyol fatty acid partial esters, portion of the fatty acid esters and an effective amount of a basic catalyst- ..The polyol can also be an alkoxylated polyol having three or more hydroxy groups.

Figure 1:
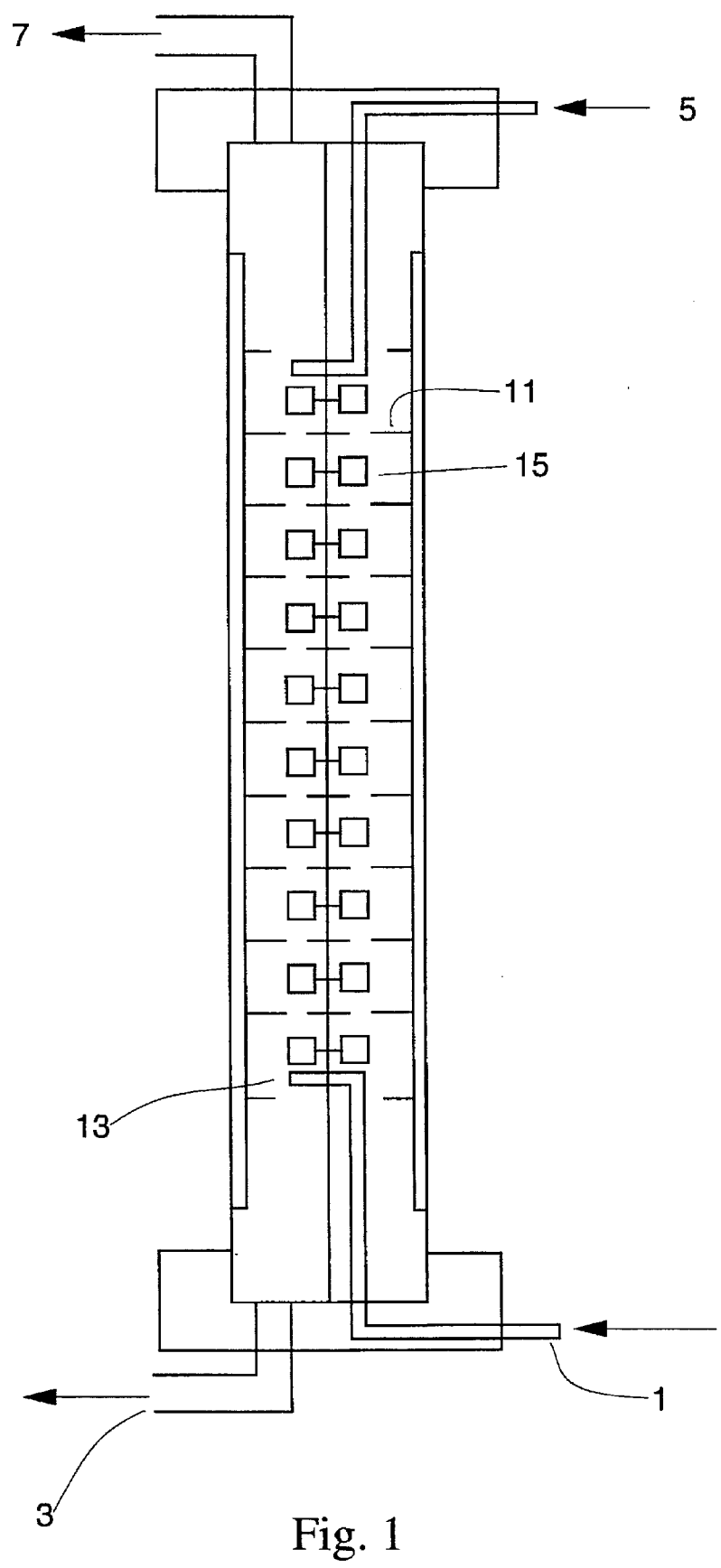
FIG. 1 shows a typical reactive adsorption column and the flow of the materials into the reactor. A variety of column internals can be used. The illustrated column uses interstage baffles (11) to control the flow of the triglyceride, and agitation (15) to produce intimate contact of gas and liquid phases
Figure 2:
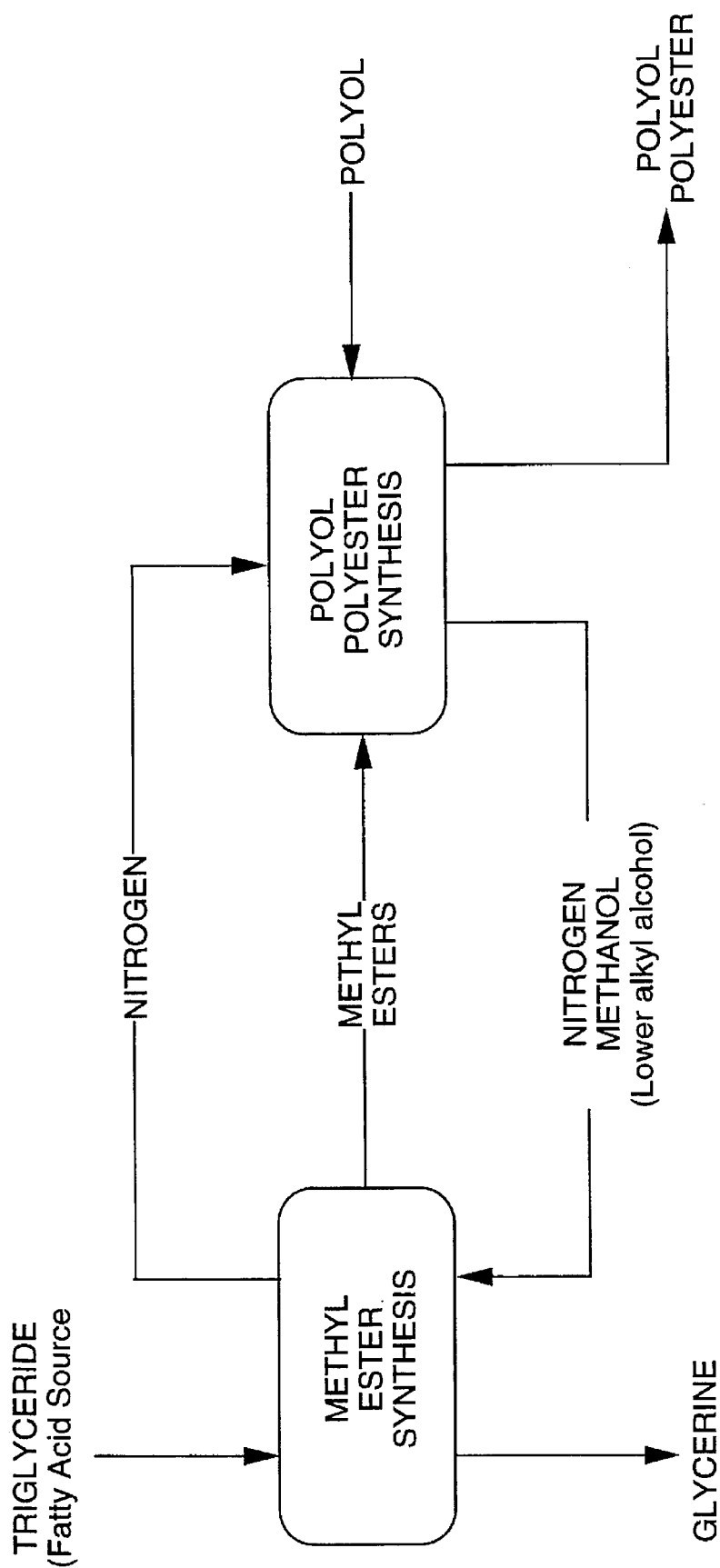
FIG. 2 is block diagram of the process.

All percentages herein are by weight unless otherwise indicated.

DETAILED DESCRIPTION OF THE INVENTION

The process is described in detail by referring to methyl esters and methyl alcohol since these are the most commonly used lower alkyl group. However, it should be readily understood that any lower alkyl alcohol can be used. By lower alkyl alcohols is meant the $C_1$-$C_6$ alcohols, including all of their isomers. Only monoalchols are used.

The process is exemplified with triglycerides as the fatty acid source, but any natural or synthetic source of fatty acid esters can be used in the place of the triglyceride. For example, diglycerides, glycol esters, waxes or other sources can be used. Triglyceride is the preferred source since it is readily available, a renewable resource, and relatively inexpensive. Marine and fish oils are good sources of polyunsaturated fatty acids, vegetable oils and animal fats and oils are sources of saturated and unsaturated fatty acids. These fats and oils can be fractionated and selectively hydrogenated to produce the desired fatty acids for the formation of the methyl or alkyl esters.

Suitable preferred saturated fatty acids include, for example, acetic, butyric, caproic, caprylic, capric, lauric, myristic, palmitic, stearic, arachidic, behenic, isomyristic, isomargaric, hydroxystearic, and anteisoarachadic. Suitable preferred unsaturated fatty acids include, for example, myristoleic, palmitoleic, ricinoleic, linoleic, oleic, elaidic, linolenic, eleosteric, arachidonic, erucic, and erythrogenic acids. The fatty acids can be used "as is," and/or after hydrogenation, and/or isomerization, and/or purification.

Preferred sources of the fatty acids are vegetable oils, hydrogenated vegetable oils, marine oils, and animal fats and oils. Preferred vegetable oils include corn oil, canola oil, olive oil, cottonseed oil, soybean oil, sunflowerseed oil, high erucic acid rapeseed oil, partially or fully hydrogenated soybean oil, partially or fully hydrogenated canola oil, partially or fully hydrogenated sunflowerseed oil, partially or fully hydrogenated high erucic acid rapeseed oil, and partially or fully hydrogenated cottonseed oil.

As used herein, the term "gaseous stream" is meant to encompass the alcohol and inert gas mixture that is used in the reaction. This stream is a by product of the polyol polyester synthesis step below. Nitrogen, carbon dioxide, helium or other inert gas can be used in this reaction. Nitrogen is preferred due to its ready availability and cost. Steam or water is not acceptable since the water will neutralize the catalyst and can hydrolyze both the triglycerides and the methyl esters that are formed.

Polyol Polyester Synthesis Step

The second step of the process of the present invention comprises transesterification of a fatty acid methyl ester and a polyol. This transesterification reaction can occur in a one step or two step process which can be solvent-based or solvent-free (See, for example, U.S. Pat. No. 4,954,621 (Masaoka et al.); U.S. Pat. No. 4,968,791, (Van Der Plank), issued Nov. 6, 1990; U.S. Pat. No. 5,079,355 (Meszaros Grechke et al.) issued Jan. 7, 1992; or U.S. Pat. No. 5,071,975 (Ver der Plank et al.) issued Dec. 10, 1991, herein incorporated by reference). Preferably the transesterification reaction is a solvent-free two stage transesterification reaction in which polyol fatty acid polyesters.

When a two stage solvent-free esterification reaction is used, polyol fatty acid partial esters are first formed from a heterogeneous reaction mixture containing a polyol, at least a portion of the required amount of fatty acid methyl esters, an effective amount of a basic esterification catalyst, and optionally, but, preferably, an emulsifier to improve contact between the polyol (sucrose) and the methyl esters such as soap and/or sucrose partial esters. Raw materials which are substantially free of glycerine and monoglyceride are preferably selected for use herein.

As used herein, the term "polyol" is intended to include any linear, cyclic, or aromatic compound containing at least four free esterifiable hydroxyl groups or an alkoxylated linear, cyclic or aromatic compound having at least three free esterifiable hydroxyl group. Suitable polyols include monosaccharides such as, mannose, galactose, arabinose, xylose, ribose, apiose, rhamnose, psicose, fructose, sorbose, tagitose, ribulose, xylulose, and erythrulose; oligosaccharides such as, maltose, kojibiose, nigerose, cellobiose, lactose, melibiose, gentiobiose, turanose, rutinose, trehalose, sucrose and raffinose, and polysaccharides amylose, glycogen, cellulose, chitin, inulin, agarose, zylans, mannan and galactans can also be used in the process of the present invention. The sugar alcohols most widely distributed in nature and suitable for use herein are sorbitol, mannitol and galactitol. The alkoxylated polyols include ethoxylated glycerine having an average of 3 to 15 ethoxy groups and propoxylated glycerine (See U.S. Pat. No. 5,389,932 issued Feb. 14, 1995 and U.S. Pat. No. 4,861,613 issued Aug. 29, 1989 for examples of suitable alkoxylated compounds).

Particularly preferred classes of materials suitable for use herein include monosaccharides, the disaccharides and sugar alcohols. Preferred carbohydrates and sugar alcohols include xylitol, sorbitol, and sucrose. The most preferred is sucrose.

The use of a small particle size polyol, e.g., sucrose, in esterification reactions to form polyol polyesters is highly desirable to improve the speed of reaction. An improved reaction can be achieved without the use of solvent, either in a preliminary step, or in the reaction itself, if the particle size of the solid polyol is less than about 100 microns, preferably less than about 50 microns, more preferably less than about 10 microns. These particle sizes can be achieved, for example, by a combination of grinding, milling, and/or sieving.

Alkali metal soaps are typically, and preferably, used as emulsifiers in this process described herein. For solid polyols, like sucrose, such soaps are believed to be essential. As used herein, the term "alkali metal fatty acid soap" includes the alkali metal salts of saturated and unsaturated fatty acids having from about 8 to about 22 carbon atoms, preferably from about 8 to about 18 carbon atoms. Accordingly, suitable alkali metal fatty acid soaps include, for example, the lithium, sodium, potassium, rubidium, and cesium salts of the fatty acids described above. Mixtures of fatty acids derived from soybean oil, sunflower oil, safflower oil, and corn oil are preferred. Accordingly, preferred alkali metal fatty acid soaps include the potassium soap made from soybean oil fatty acids.

Although some level of soap is typically necessary for optimal performance, especially with solid polyols (e.g. sucrose), the absolute level of soap is desirably kept low, even when there is another emulsifier present. The level of soap should be at least enough to dissolve the polyol at an acceptable rate. Therefore, the level of soap can be reduced as a result of using smaller particle polyol, e.g., sucrose, and/or reaction conditions that favor the solubilization of the polyol. Too much soap can cause excessive foaming. The level of soap in the first stage of the reaction is desirably from about 0.001 to about 0.75, preferably from about 0.1 to about 0.4 moles of soap per mole of polyol. The soap is preferably used in combination with another emulsifier, preferably with the lower esters of the polyol and the fatty acid which are present either by being added as part of the initial reaction mixture, or by backmixing. Also, the soap is preferably potassium soap of hydrogenated fatty acids containing from about 8 to about 22 carbon atoms.

Like the fatty acid ester reactants, it is also highly desirable that the soap contain little or no difatty ketones and/or β-ketoesters. These by-products can form in the soap as the result of contact with basic reagents, such as potassium hydroxide, used during saponification. Preferably, the soap contains about 10 ppm or less difatty ketones and/or β-ketoesters.

Suitable basic catalysts for use in preparing the polyol fatty acid polyesters described in the present invention include alkali metals such as sodium, lithium and potassium, alloys of two or more alkali metals, such as sodium-lithium and sodium-potassium alloys; alkali metal hydrides, such as sodium, lithium and potassium hydride; alkali metal lower ($C_1$–$C_4$) alkyls such as butyl lithium; and alkali metal alkoxides of lower ($C_1$–$C_4$) alcohols, such as lithium methoxide, potassium t-butoxide, potassium methoxide, and/or sodium methoxide. Potassium methoxide is preferred, especially when used with potassium soap. Certain basic catalysts, such as sodium and potassium hydride, are particularly prone to generate difatty ketones and/or β ketoesters.

Another particularly preferred class of basic catalyst includes potassium carbonate, sodium carbonate, barium carbonate, or mixtures of these compounds having particle sizes that are less than about 100 microns, preferably less than about 50 microns, as discussed more fully hereinafter. It has been found that when these specific compounds are used as catalysts, increased yields of light colored higher polyol polyesters are obtained when compared to essentially identical reactions carried out using more conventional catalysts, such as sodium hydride, potassium hydride, soap, or sodium methoxide. These preferred catalysts can also be used in admixture with the more conventional basic catalysts, described above. Potassium carbonate and/or potassium methoxide are the most preferred catalysts for use herein. The use of these catalysts is further disclosed in U.S. Pat. No. 4,517,360 (Volpenhein), issued May 14, 1985, which is incorporated herein by reference.

More reactive catalysts such as potassium or sodium methoxide can be protected until their addition into the reaction mixture. Preferably the catalyst should be suspended in or more preferably encapsulated by a material that will either be present in the reaction mixture or be readily separated from the reaction mixture. Suitable encapsulating agents include said alkyl esters of, e.g., $C_{16}$–$C_{22}$ fatty acids. (As described hereafter, these catalysts can also be protected when prepared from and stored in a lower ($C_1$–$C_4$) alcohol, such as methanol, under anhydrous conditions.) Addition of these more alkaline, reactive catalysts in the second stage of the reaction after the polyol has an average degree of esterification of more than about 60%, preferably more than about 85%, provides improved reaction kinetics and results in a greater degree of esterification of the polyol yet does not create the level of color/odor materials that would be created if such catalysts were present from the start of the reaction.

The level of catalyst is kept as low as possible, particularly in the second stage of the reaction, as discussed more fully hereafter, typically in the range of from about 0.01 to about 0.5, preferably from about 0.01 to about 0.1, more preferably from about 0.02 to about 0.05, moles of catalyst per mole of polyol. The level of catalyst can be lowered to the least amount that is effective to give a reasonable rate of reaction. It is possible to have very fast reactions using only the residual base in, e.g., the soap emulsifier commonly used in such reactions. It is desirable to keep the level of base as low as possible to minimize formation of color and/or odor bodies and/or excess soap and/or by-products. It is also desirable to effect the removal of oversize catalyst after the first stage of the reaction, and/or the destruction and removal of the catalyst after the reaction has reached the desired end point.

Typically, the molar ratio of the fatty acid methyl esters to the polyol ranges from about 8:1 to about 13.5:1. If soap is used as an emulsifier, the molar ratio of the soap to the polyol typically ranges from about 0.08:1 to about 0.75:1. If sucrose partial esters are used as emulsifiers, they can be added to the starting mixture at a level of 1% to 50% by weight, preferably 5% to 30%, more preferably 10% to 20%. Combinations of sucrose esters and soap can be used advantageously. The ratio of catalyst to the polyol typically ranges from about 0.02:1 to about 0.2:1. The precise ratio of these reactants can be freely selected from within the guidelines previously described. However, some routine experimentation can be necessary in order to establish the optimum ratios for a given set of reactants. The first stage reaction mixture can be formed in a solvent-free manner or by using a solvent such as water to dissolve one or more of the reactants (e.g., sucrose), followed by removal of the solvent before carrying out the first stage reaction.

This first stage reaction mixture is then heated to an appropriate temperature to provide a melt in which the polyol and the fatty acid methyl esters react to form polyol fatty acid partial esters. As used herein, the term "polyol fatty acid partial esters" are those esters of the polyol wherein up to about 50% of the hydroxy groups of the polyol have been esterified. In the case of sucrose, the primary sucrose fatty acid partial esters are the mono-, di- and/or triesters. The end of the first stage of the reaction is usually determined by measuring the level of unreacted polyol in the reaction mixture. In the case of sucrose, the end of the first stage typically occurs when the level of unreacted sucrose is less than about 1%.

This first stage reaction mixture is typically heated to temperatures of from about 265° to about 285° F. (from about 129.4° to about 140.6° C.), preferably to from about 270° to about 275° F. (from about 132.2° to about 135° C.). These reaction temperatures typically achieve a rapid initial esterification of the polyol to form the polyol fatty acid partial esters without excessive degradation of the polyol. The first stage reaction is also desirably carried out with an inert gas sparge such that the partial pressure of methanol is from about 1 to about 100 mm Hg, preferably from about 5 to about 50 mm Hg.

If soap is the emulsifier, after the average degree of esterification reaches about 60%, the soap emulsifier is no longer needed to facilitate the reaction and, therefore, can be removed. The soap emulsifier is not essential after the polyol has reacted once and there is sufficient partial ester to maintain the homogeneity of the reaction mixture. Removal of soap can be accomplished, e.g., by filtration, centrifugation, etc., since the soap is relatively insoluble in the reaction mixture at higher degrees of esterification. The filtered reaction mixture typically has a soap level of less than about 0.5, preferably less than about 0.1 moles of soap per mole of polyol, more preferably less than about 0.05 moles of soap per mole of polyol. The material filtered out of the reaction can be used as a reactant in the first stage reaction mixture. However, since the composition of this material can vary, it is usually better not to recycle it.

Unreacted polyol and/or large particle catalyst are also desirably removed from the reaction mixture via filtration and/or centrifugation.

In the second stage of the solvent-free transesterification reaction, highly esterified polyol fatty acid polyesters are formed from a reaction mixture containing the polyol fatty acid partial esters, the remaining portion of the fatty acid methyl esters, and an effective amount of a basic catalyst. This remaining portion of the fatty acid methyl esters can be obtained by including an excess thereof in the first stage reaction mixture, i.e., an amount beyond that required to form polyol fatty acid partial esters ("singlestep" addition). However, the remaining portion of the fatty acid methyl esters required to obtain highly esterified polyol fatty acid polyesters is typically added to the reaction mixture resulting from the first stage of the reaction ("two-step" addition).

The reaction mixture resulting from the first stage of the reaction can contain sufficient basic catalyst for the purposes of the second stage of the reaction. However, more basic catalyst can be added, if needed. This additional basic catalyst can be the same as the basic catalyst used in the first stage of the reaction, or can be a different basic catalyst.

During the second stage of the reaction, the polyol fatty acid lower esters and the remaining portion of the fatty acid esters react to provide highly esterified polyol fatty acid polyesters. As used herein, the term "highly esterified polyol fatty acid polyesters" refers to a polyol wherein at least about 50%, preferably at least about 70%, and most preferably at least about 96%, of the hydroxy groups are esterified. In the case of highly esterified sucrose polyesters, this typically refers to the hexa-, hepta-, and particularly octa- esters. For example, if at least about 96% of the hydroxy groups of sucrose are esterified, at least about 70% of the sucrose esters are sucrose octaesters.

During both of these stages an inert gas sparge is used to remove the lower alkyl alcohols as they are formed and to prevent oxidation reactions from occurring. This inert gas/lower alkyl alcohol stream becomes a feed stream for the methyl ester synthesis described below.

Methyl Ester Synthesis

Triglyceride is converted into the methyl ester or lower alkyl ester by the following process:

Triglyceride is contacted with a gaseous stream of nitrogen or other inert gas and lower alkyl alcohol in a batch reactor or preferably in a continuous reactive adsorption column. The methanol comprises from 1 to 10% of the gaseous stream. The partial pressure of the alcohol in the gaseous stream affects the solubility of the alcohol and drives the reaction. Therefore, the concentration of the alcohol in the inert gas as well as the temperature and pressure of the entering gas/alcohol stream are important. The gas/methanol stream enters the column at (1) and is dispersed through the spray sparge ring (13). The flow rate of the gaseous stream, i.e., the nitrogen alcohol mixture, as it enters the column is from about 0.1:1 to about 7.5:1 (weight basis) relative to the triglyceride flow.

The exact shape and structure of the sparge devices are not critical to the reaction, and its configuration is easily determined by one skilled in the art. What is important is that the inert gas/alcohol stream be dispersed in the triglyceride in a manner that it contacts the triglyceride effectively allowing the alcohol to be absorbed by and react with the triglyceride, and thus to convert the fatty acids to alcohol esters.

For maximum conversion of triglyceride to alkyl ester, a molar excess of alcohol is used; in the range of 3 moles of alcohol to one mole of triglyceride up to a ratio of about 15:1. This represents a 1 to 5 fold ratio of alcohol to fatty acid group. For maximum removal of methanol from the nitrogen stream, an excess of triglyceride is used. In this case, the alcohol to triglyceride ratio is from 0.1:1 to about 3:1. Under preferred conditions, both high methyl ester conversion and high alcohol removal are achieved.

The triglyceride or other fatty acid source is mixed with an esterification catalyst and added to the reactor. In a counter current column reactor, it enters at 3 and flows down the column. The column contains a material that disperses nitrogen or inert gas and methanol in the triglyceride. Packing or agitated stages 15 are preferred as shown in FIG. 1. Other columns such as tray columns, perforated disk columns, and bubble columns can be used. The exact type of column that is used is not critical and depends on a number of factors which are readily apparent to one skilled in the art.

The nitrogen and methyl alcohol can be contacted with the triglyceride in a variety of ways including a counter current, cocurrent or batch systems. Counter current is the preferred method.

Suitable basic catalysts for use in preparing the methyl esters used in the process of the present invention include alkali metals such as sodium, lithium and potassium; alloys of two or more alkali metals, such as sodium-lithium and sodium-potassium alloys; alkali metal hydrides, such as sodium, lithium and potassium hydride; alkali metal lower ($C_1$–$C_4$) alkyls such as butyl lithium; and alkali metal alkoxides of lower ($C_1$–$C_4$) alcohols, such as lithium methoxide, potassium t-butoxide, potassium methoxide, and/or sodium methoxide.

The preferred catalyst is a basic catalyst e.g., an alkali or alkaline earth metal hydroxide, alkoxide or carbonate. Preferably the reaction is catalyzed by sodium or potassium alkoxide corresponding to the lower alkyl alcohol. When methanol is the lower alkyl alcohol, sodium or potassium methoxide is used. Alkali metal alkoxides are readily available commercially or can be prepared by reaction potassium or sodium with an excess of the alcohol. The most preferred catalysts are sodium or potassium methoxide or potassium carbonate. Acid catalysts such as, p-toluenesulfonic acid, phosphoric acid, potassium or sodium mono or dihydrogen phosphate, hydrochloric acid or sulfuric acid can also be used. The catalyst is typically used at a level of from about 0.1% to about 1.0% of the triglyceride (weight basis).

As mono- and diglycerides form, they facilitate the reaction and create a foam. The time of the reaction can vary from 5 minutes to 5 hours preferably, from ½ to 2 hours. The exact time depends on the size of the reaction vessel as well as the flow rate of the materials, the temperatures and the pressure.

In a reaction column, triglyceride is added to the reaction vessel along with the catalyst. Nitrogen and methyl alcohol from a polyol polyester transesterification is passed through the column and contacted with triglyceride. A preferred source of this gas stream is the transesterification synthesis reaction of polyol polyesters using methyl esters as the fatty acid source. The gas stream is mixed with triglyceride in a ratio of about 15 moles of alcohol to each mole of triglyceride to about 3 moles of lower alkyl alcohol per mole triglyceride. This makes the reaction proceed so that the majority (from 80% to 95%) of the triglyceride is converted into methyl esters.

When this reaction is used to cleanse the inert gas stream, the molar ratio of alcohol to triglyceride is from 0.1:1 to about 3:1.

The reaction temperature is between about 20° C. and about 100° C. The pressure is preferably atmospheric or above atmospheric. Generally, the reaction is run at between 14 psia to about 150 psia. The preferred level of pressure for introducing the methanol is in the range of 14.7 psia to 125 psia, and more preferably 35 to 100 psia.

The esters and glycerine and any monoglycerides or diglycerides are recovered from the bottom of the column as a mixture with any unreacted triglyceride. In the counter current column reactor, they exit through 3. The mixture is first separated by settling or by centrifugation wherein the glycerine is also separated from the mixture.

Optionally, additional methanol or alcohol can be added to drive the reaction to completion. In this case, a glycerine separation step is required.

The catalyst and remaining glycerine are removed by water washing of the crude reaction mixture. The catalyst and the glycerine dissolve in the water and the esters are removed by settling or centrifugation. The clean up of the crude reaction mixture is accomplished by conventional processing.

The methyl esters are then separated or purified by distillation or other conventional means. The methyl esters can be further purified by fractionation, including molecular distillation, if desired.

The inert gas used in this reaction is preferably that recovered from the polyol polyester transesterification reaction.

The nitrogen exiting this reaction is typically less than 2000 ppm methanol or alcohol and can be as low as 50 ppm alcohol. The lower levels of residual methanol or alcohol in nitrogen are reached with excess triglycerides. The nitrogen exhaust is then used to sparge the polyol polyester process.

The following examples illustrate this invention, but are not intended to limiting thereof. Examples 1 to 3 are intended to show that you can reach very low levels of residual alcohol in nitrogen (50 ppm to 520 ppm) at a wide range of pressures (15 psig or 85 psig) with stoichiometric excess of triglyceride. Conversion to methyl esters was low in each case (about 20%).

EXAMPLE 1

| INGREDIENTS | AMOUNT |
| --- | --- |
| soybean oil | stoichiometric excess (52 lb/hr) |
| sodium methoxide | 0.05 moles/mole oil |
| nitrogen | 32 lb./hr. |
| methanol | 4.0 gm./min. (1.6% of $N_2$) |

In a continuous multi-stage agitated column triglyceride (refined, bleached and deodorized soybean oil) containing sodium methoxide is fed continuously into the top of the reactor. The reactor is 6" in diameter by 48" tall and has 10 agitated stages. The agitator was run at about 1500 rpm. The column was configured as in FIG. 1. The triglyceride is passed countercurrent to a methanol/nitrogen stream fed from the bottom of the reactor. The reactor is held at 38° C., and 64.7 psia (50 psig). The nitrogen/methanol flow is 32 lb./hr. The product nitrogen stream contains 40 ppm methanol. This nitrogen stream is used in the polyol polyester synthesis described in Example 6.

EXAMPLE 2

In a reaction similar to Example 1, the nitrogen gas stream containing 1.6% methanol derived from a polyol polyester synthesis and is passed through the column at 52 lb./hr. Triglyceride containing 0.05 moles solid sodium methoxide per mole triglyceride is fed into the top of the column at 52 lb./hr. The temperature is 43° C. and the pressure is 99.7 psia. The exhaust nitrogen has 80 ppm methanol in it.

EXAMPLE 3

Reactive absorption is carried out in a continuous, counter-current, multi-stage agitated column. Triglyceride is continuously fed into top of reactor and product drawn at bottom. Nitrogen/methanol fed into bottom of reactor and discharged at top. A stoichiometric excess of triglyceride is used.

Conditions

Liquid Feed—52 lb./hr. catalyzed triglyceride (0.05 moles solid NaOCH$_3$ per mole triglyceride)

Gas Feed—32 lb./hr. nitrogen, 4.0 grams/min. methanol (1.6% MeOH)

Temperature—98° F. (37° C.)

Pressure—15 psig (29.7 psia)

Results 520 ppm (0.052%) methanol in exhaust nitrogen.

EXAMPLE 4

Reactive absorption is carried out in a continuous, counter-current, multi-stage agitated column as in the previous examples. Triglyceride is continuously fed into top of reactor and product drawn out the bottom. Nitrogen/methanol is fed into bottom of reactor and discharged at top. Roughly stoichiometric amounts of triglyceride and methanol are used.

Conditions

Liquid Feed—80 lb./hr. catalyzed triglyceride (0.15 moles solid NaOCH$_3$ per mole triglyceride)

Gas Feed—200 lb./hr. nitrogen, 7.8 lb./hr. methanol

Temperature—130° F. (54° C.)

Pressure—65 psig (79.7 psia)

Results 2000 ppm (0.20%) methanol in exhaust nitrogen

81% conversion of triglyceride to methyl esters

EXAMPLE 5

A reactive absorption conversion of triglyceride to methyl esters is carried out in a 1.5 liter batch agitated reactor. A stoichiometric excess of methanol is bubbled through catalyzed triglyceride.

Conditions

Liquid—883 grams of triglyceride, 3.05 grams of sodium methoxide catalyst

Gas—1.6 liters/min. nitrogen, 2.1 grams/min. methanol

Temperature—194° F. (90° C.)

Pressure—atmospheric (14.7 psia)

Results

55% conversion of triglyceride to methyl esters in 30 minutes.

80% conversion to methyl esters in 75 minutes.

Reaction mixture at 80% conversion is allowed to stand resulting in a two phase system. The heavier phase (primarily glycerine) is removed. The remaining mixture was further reacted under conditions similar to those described above for 75 minutes, leading to 96% methyl esters in the final product. These methyl esters are purified and then used in a synthesis as described in Example 6.

EXAMPLE 6

Methyl ester (1,317 lbs.) is mixed with 200 lbs. of potassium stearate, 300 lbs of granular sucrose and 12 lbs. of granular potassium carbonate in a 750 gallon reactor for 7.5 hours at a temperature of 135° C. with a nitrogen sparge to keep the partial pressure of methanol below 10 mm Hg. Additional methyl ester (2,095 lbs.) and granular carbonate (12 lbs.) are added to the reactor and mixed for another 5 hours at 135° C. while maintaining a methanol partial pressure of less than 4 mm Hg until the composition of the polyol polyester is 74.9% octaester, 24.8% heptaester and 0.25% hexaester and below. The nitrogen gas with methanol is sent to a reactive absorption vessel as described in Example 1.

The soap is removed by adding 211 lbs. if deionized water at 77° C. in a 750 gallon stirred tank reactor and centrifuging. Color and lower levels of soap are removed by water washing with 629 lbs. of deionized water at 77° C. in a stirred tank reactor for 10 minutes at low rpm. The water is settled for one hour by gravity and then drained from the bottom of the reactor. The product is dried by reducing the pressure to <10 mm Hg and maintaining the temperature at 65°–80° C. Silica gel (35 lbs.) is mixed with the dry product at 77° C. for 30 minutes. The silica gel is removed in a filter press and the product is then evaporated at a temperature of 235° C. (455° F.) at a pressure 1.0 mm Hg, and finally steam stripped with 10% steam in a packed column at a temperature of 235° C. (455° F.) and a pressure of 2 mm Hg.

EXAMPLE 7

About 200 g/min of feed comprised of 9% sucrose, 85.0% methyl esters, 1% potassium methoxide catalyst, and 5% potassium stearate is fed into a continuous reactor. About 400 g/min of nitrogen is fed into the bottom of the reactor. The temperature is maintained at roughly 275° F. and pressure is roughly atmospheric. The reaction proceeds to about 97% conversion of sucrose to sucrose polyester. The effluent nitrogen stream contains about 3% methanol. This nitrogen stream is compressed to 65 psig, cooled to below 100° F., and fed into the bottom of a reactive absorption column. About 140 g/min triglyceride with 1 g/min NaOCH$_3$ catalyst is fed into the top of this column and reacts to form methyl esters as described in EXAMPLE 4. The reactive absorption column is maintained at about 100° F. The triglyceride is converted to about 80% methyl esters while methanol is simultaneously removed from the nitrogen stream. The exiting nitrogen stream contains about 2000 ppm methanol. This nitrogen stream is then recycled to the first reactor. The methyl esters produced in the second reaction are further reacted with excess methanol to achieve about 99% conversion. The esters are then washed 3 times with 10% by weight water and fractionated in a wiped film evaporator. The fractionated methyl esters become part of the feed material to the first continuous reactor.

What is claimed is:

1. A process for preparing a polyol fatty acid polyester, which process comprises the steps of:

A. preparing a fatty add alkyl ester by:
   1) contacting a fatty acid source with an intimate mixture of an inert gas and a lower alkyl alcohol at a temperature of between about 20° C. to about 100° C., at a pressure of from about 14 to about 150 psia in the presence of a catalyst;
   2) reacting the fatty acid source with the lower alkyl alcohol to form the fatty acid alkyl ester; and B. transesterifying the fatty acid alkyl ester and a polyol in a solvent-free two-stage process wherein a first stage comprises forming a polyol fatty add partial ester and a lower alkyl alcohol from a reaction mixture containing a polyol and at least a portion of the fatty acid alkyl ester in the presence of an effective mount of a basic catalyst and optionally an effective mount of soap emulsifier, and a second stage comprises forming a highly esterified polyol fatty acid polyester and additional lower alkyl alcohol from a reaction mixture containing the polyol fatty acid partial ester, the remaining portion of the fatty acid alkyl ester and an effective mount of a basic catalyst, wherein, both stages are conducted in the presence of an inert gas, and the lower alkyl alcohol formed in the first stage and the second stage is removed by and contained in the inert gas, thereby forming the intimate mixture of the inert and the lower alkyl alcohol which is recycled to and used in step (A).

2. A process according to claim 1 wherein the preparation of fatty acid alkyl ester is conducted at a pressure between about 30 psia and about 100 psia.

3. A process according to claim 2 wherein the catalyst in both steps is selected from the group consisting of sodium methoxide, sodium alkoxide, potassium alkoxide, sodium carbonate, potassium carbonate, and mixtures thereof.

4. A process according to claim 1 wherein the inert gas is nitrogen.

5. A process according to claim 1 wherein the lower alkyl alcohol is methanol and the inert gas is nitrogen.

6. A process according to claim 1 wherein the fatty acid source is a triglyceride selected from the group consisting of vegetable oils, hydrogenated vegetable oils, marine oils, and animal fats and oils.

7. A process according to claim 6 wherein the triglyceride is selected from the group consisting of canola oil, olive oil, cottonseed oil, soybean oil, sunflowerseed oil, high erucic acid rapeseed oil, partially or fully hydrogenated soybean oil, partially or fully hydrogenated canola oil, partially or fully hydrogenated sunflowerseed oil, partially or fully hydrogenated high erucic acid rapeseed oil, partially or fully hydrogenated cottonseed oil, and mixtures thereof.

8. A process according to claim 7 wherein the molar ratio of lower alkyl alcohol to triglyceride is about 0.1:1 to about 15:1.

9. A process according to claim 8 wherein the preparation of fatty acid alkyl ester in Step (A) is conducted in a reaction column.

10. A process according to claim 9 wherein the reaction column is selected from the group consisting of packed columns, tray columns, perforated disk columns, bubble columns and agitated columns.

11. A process according to claim 1 wherein the polyol is a sugar or a sugar alcohol.

12. A process according to claim 11 wherein the level of the soap emulsifier in step (B) is from about 0.01 to about 0.75 moles per mole of the polyol.

13. A process according to claim 1 wherein the inert gas of Step (A) is nitrogen and is recycled from step (A) to steep (B).

14. A process according to claim 12 wherein the lower alkyl alcohol is methanol and the polyol is sucrose.

15. A process according to claim 11 wherein the fatty acid source is a triglyceride selected from the group consisting of vegetable oils, hydrogenated vegetable oils, marine oils, and animal fats and oils.

16. A process according to claim 13 wherein the molar ratio of the fatty acid esters to the polyol is from about 8:1 to about 13.5:1.

17. A process according to claim 16 wherein the molar ratio of the lower alkyl alcohol to the triglyceride in step (A) is about 0.1:1 to about 15:1.

18. A process according to claim 11 wherein the temperature of Step (B) is from about 129.4° C. to about 140.6° C.

19. A process according to claim 18 wherein the methanol in Step (B) in the intimate mixture has a partial pressure of from about 1 to about 100 mm Hg.

* * * * *